United States Patent [19]
Palmer et al.

[11] Patent Number: 4,622,035

[45] Date of Patent: Nov. 11, 1986

[54] BOOT WITH CONTINUOUS MEDICAMENT SUPPLY

[76] Inventors: Betty Palmer, 3064 Towerway Dr., Chattanooga, Tenn. 37406; Norman E. Reitz, P.O. Box 2630, Menlo Park, Calif. 94026

[21] Appl. No.: 693,874

[22] Filed: Jan. 23, 1985

[51] Int. Cl.⁴ ............................................. A61M 35/00
[52] U.S. Cl. ..................................... 604/293; 604/289
[58] Field of Search ................. 128/382, 19, 581, 133, 128/382, 399–403, 65–67; 604/289, 290, 293; 36/3 R

[56] References Cited

U.S. PATENT DOCUMENTS

| | | | |
|---|---|---|---|
| 2,676,422 | 4/1954 | Crawford | 36/3 R |
| 2,703,937 | 3/1955 | McGinn | 36/3 R |
| 3,749,091 | 7/1973 | Basa | 604/293 |
| 3,905,367 | 9/1975 | Dapcich | 604/293 |

Primary Examiner—C. Fred Rosenbaum
Assistant Examiner—J. L. Kruter
Attorney, Agent, or Firm—Norman E. Reitz

[57] ABSTRACT

A boot is provided for the therapeutic or cosmetic treatment of the human foot. The boot has an impervious outer covering and includes a medicament supply network which provides a continuous supply of medicament to an absorbent lining around the inside of the outer covering. The medicament supply network contains a medicament reservoir located adjacent the opening of the boot and a series of supply fingers which extend along the inside of the contours of the outer covering to the extremities of the boot. A medicament of choice may be continuously supplied through the medicament supply network and transferred by the absorbent lining to the skin of the foot of the wearer.

8 Claims, 9 Drawing Figures

U.S. Patent    Nov. 11, 1986    4,622,035
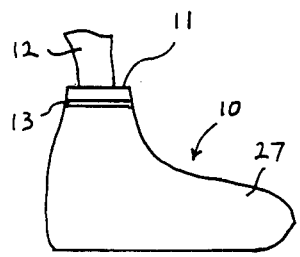
FIG. 1
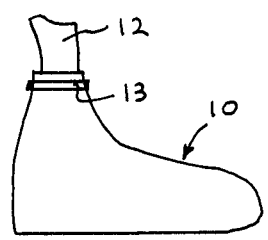
FIG. 2
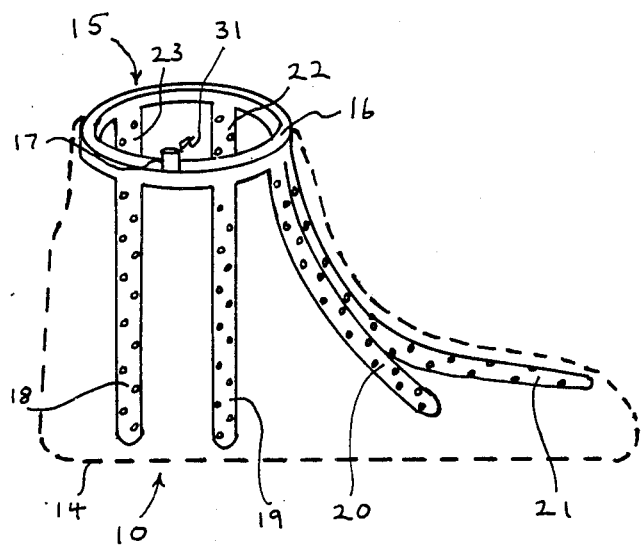
FIG. 3
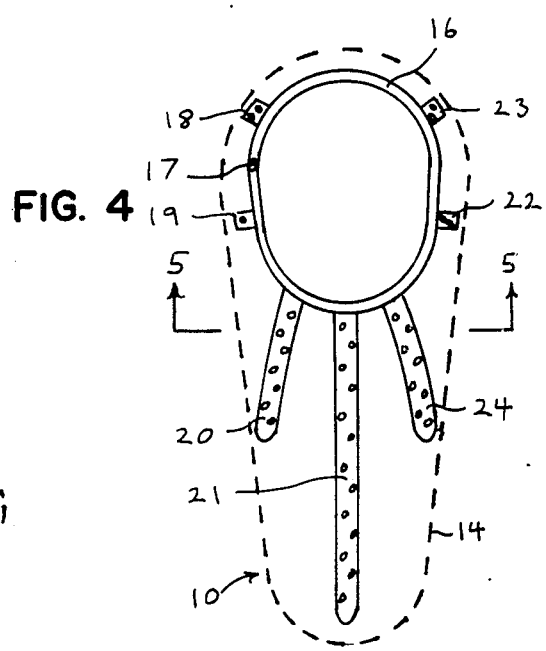
FIG. 4
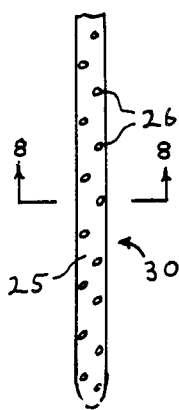
FIG. 7
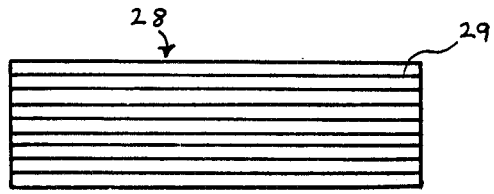
FIG 8
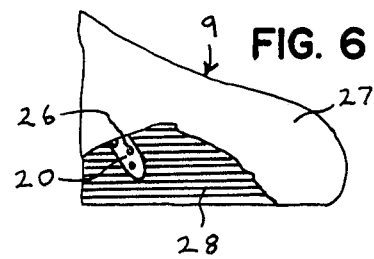
FIG. 6
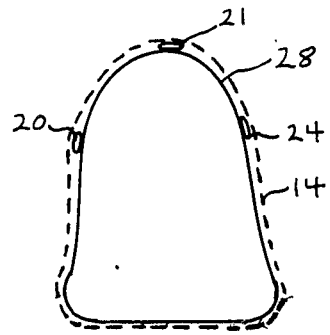
FIG. 5
FIG. 9

BOOT WITH CONTINUOUS MEDICAMENT SUPPLY

This invention relates to footwear for providing therapeutic treatment to the feet and, more particularly, relates to a boot having an absorbent inner lining and a means to supply a therapeutic lotion to the lining while the boot is being worn.

Various aliments afflict the feet. Many of them, such as callouses, corns, rashes, thick hard toe nails, scaley skin, athlete's foot and dry skin around the heel may be successfully treated by the application of therapeutic lotions, creams, mud packs, poultices and like compositions. Hydrotherapy is also effective in stimulating the inherent healing powers of the body. Traditionally, however, these treatments have required the patient to devote periods of time exclusively to receiving treatment. Often they have required the person receiving treatment to travel to a particular location or establishment where treatment is provided, at times with the assistance and associated cost of an attendant or therapist.

Remedies for foot ailments are commonly available. Often, however, they only treat the symptoms and do not fully cure the ailment. Customized shoes, foot pads, sponge rubber stick-on pads for corns and callouses and similiar items may make standing or walking more bearable but do not address the problem at the source. What is required is to both treat the symptoms and eliminate the source of the problems. This is accomplished in the first instance by restoring the foot to a state of health in all its aspects: skeletal, cardiovascular, muscular and dermatalogical. Since there is no known way to isolate the effects of internally administered substances specifically and exclusively to the feet, the best way to treat the foot and restore it to health is through the skin. Yet such treatments are not always convenient or without inordinate expense, as described previously.

Various devices have been proposed for the dermatological treatment of the feet. In H. R. Lewis, "Medical Slipper", U.S. Pat. No. 2,664,087, a liquid-tight slipper is provided for holding a medicinal solution into which the foot is dipped. The inner surface of the slipper is impregnated with paraffin to make it watertight. As a consequence, a portion of the foot is immersed in a pool of liquid below the liquid level and the portion of the foot above the liquid level is not exposed to the medicinal liquid at all. As a result of the use of a liquid without an absorbent lining the liquid may run out of the slipper when the wearer is in a seated or reclining posture. Also, there is no means of resupplying the liquid without removing the slipper. In J. Bronislaw de Kurowski, British Pat. No. 417,187, an impervious sheath in the shape of a stocking has an absorbent lining of sponge rubber. The sponge rubber is soaked in an emulsion for treating the foot and the sheath is placed on the foot of the person undergoing treatment. So long as the emulsion lasts the foot is treated. No means is available to replenish the emulsion. And, as with other materials previously used such as loofah or cotton wool, the sponge rubber must be inordinately thick to contain an appreciable amount of emulsion. Such a thickness would make the sheath uncomfortable to wear and would make the sheath difficult to apply to the leg or foot. Similiar devices have been proposed for use with the hand to which the previous comments are also applicable. See, S. D. Sutton, "Rubber Gloves and the Like", U.S. Pat. No. 2,916,036, and E. M. Morrison, "Glove", U.S. Pat. No. 2,653,601. And is has been proposed to include a medicament in dehydrated form within a spongy absorbent material which comprises the inside layer of a surgical dressing; see J. S. Robins, "Surgical Dressing", U.S. Pat. No. 2,858,830. Body moisture is said to liquify the medicament so it is available for a dermatological application. Here, too, the spongy material has appreciable bulk, especially when the medicament is hydrated so that it is not readily worn under the normal circumstances of life. Finally, a number of skin care articles have been proposed for applying a modest quantity of medicant or lotion to the skin. See, e.g., A. Curtay, "An Article For The Care of The Legs", Australian Pat. No. 261,676; G. Buchalter, "Article Impregnated With Skin-Care Formulations", U.S. Pat. No. 3,896,807; J. Cozza, et. al., "Treatment Device", U.S. Pat. No. 3,384,083; J. F. Migliarese, "Occlusive Medicated Sheath", U.S. Pat. No. 3,347,233; Y. Tsuneizumi, et. al., "Cosmetic Patch", U.S. Pat. No. 3,499,446; and C. H. Halley, "Beauty Mitt", U.S. Pat. No. 2,501,565. All of the above approaches to delivering a therapeutic or cosmetic lotion, cream or medicament to the skin have relatively limited capacities and do not allow the patient to select his or her own treatment. It would therefore be desirable to provide, for the care of the feet, a boot which allows the patient to select or make up a therapeutic or cosmetic lotion of her or his own choice and to continuously apply the lotion to the selected portions of the feet for prolonged periods.

It is therefore an object of the present invention to provide a liquid-tight boot for the foot which has a self-contained supply of medicament for treating the foot that can be replenished as required.

It is another object of the present invention to provide a boot which can be conveniently worn for therapeutic treatment by a person experiencing foot ailments.

It is an additional object of the present invention to provide a boot which permits the user to select and apply the medicament that will best treat his or her particular foot ailment.

It is yet another object of the present invention to provide a liquid-tight boot that has an absorbent lining that is continuously supplied with therapeutic or cosmetic lotion by a network of fingers connected to a reservoir located near the ankle area of the boot.

BRIEF DESCRIPTION OF THE DRAWINGS

For a more complete understanding of the present invention reference may be had to the accompanying drawings which are incorporated herein by reference and in which:

FIG. 1 is a pictorial side view of the therapeutic boot of the present invention after being slipped onto the foot of the wearer;

FIG. 2 is a further view from FIG. 1 after the boot has been tightened around the ankle of the wearer;

FIG. 3 is a perspective view of the boot of the present invention with the external, liquid-tight covering being shown in phantom and the medicament supply network being emphasized by bold lines;

FIG. 4 is a plan view of FIG. 3;

FIG. 5 is a cross sectional view taken through the line 5—5 of FIG. 4;

FIG. 6 is a broken-away view of the toe of the boot which illustrates the relative position of a finger of the medicament supply network behind the absorbent lining;

FIG. 7 is a detailed side view of one finger of the medicament supply network;

FIG. 8 is a cross sectional view of the finger of FIG. 7, taken through line 8—8 of FIG. 7; and FIG. 9 is a plan view of a strip of absorbent lining as used in the inside of the boot underneath the liquid-tight covering.

SUMMARY OF THE INVENTION

A boot is provided for the therapeutic or cosmetic treatment of the foot. The boot is made from a liquid-tight outer covering and may be sealed at the ankle by a strap such as a Velcro fastener. An absorbent lining covers the major portion of the interior surface. Adjacent the absorbent lining is a medicament supply network which continuously supplies a medicament to the absorbent lining and thence to the skin of the foot. The medicament supply network consists of fingers which extend from a medicament reservoir to the extremities of the interior lining. Medicament flows out from the reservoir, through the fingers and into the absorbent lining. The skin of the foot is thus continuously supplied with a medicament that is selected to treat the ailment of the wearer of the boot.

DESCRIPTION OF THE PREFERRED EMBODIMENTS

While certain general practices affect the overall state of health of the foot, there are specific substances and sequences of treatment that are preferred to therapeutically treat specific ailments. Thus, it is generally desirable to maintain skin moisture at a sufficiently high level, to avoid the use of footwear which repeatedly rubs against any part of the foot and to wear shoes that have ample arch support. But even though these practices are followed a person may suffer from ailments of the feet which require treatment. The preferred treatment may vary for each ailment. Numerous examples of substances are given in J. F. Migliarese, "Occlusive Medicated Sheath", U.S. Pat. No. 3,347,233, and in G. Buchalter, "Article Impregnated with Skin-Care Formulations", U.S. Pat. No. 3,896,807, which may be selected to treat different specific ailments. The inventors of the boot of the present invention have found that a mixture of Vitamin E, lanolin and cocoa butter efffectively treats corns, callouses and scaley dry skin. It is the aim of the therapeutic and cosmetic boot of the present invention to permit the specific dermatological treatment of all manner of foot ailments. The treating substances are prepared in a lotion of suitable viscosity and are applied through the skin of the foot as described subsequently in connection with the structure and function of the therapeutic boot of the present invention.

As seen in FIG. 1 the boot 10 is slipped over the foot of the wearer and terminates at or above the ankle and below the leg 12. The height of the boot may vary depending upon the location of the ailment, providing the principle of the invention is being practiced. For example, if the toes are being treated a low cut version will provide adequate treatment. However, if the heel or ankle are being treated a high back version may be required. When the boot 10 is placed over the foot the wearer an opening 11 exists between the leg 12 and the inside of the outer covering 27 of the boot. This opening could permit evaporation or leakage of the therapeutic or cosmetic lotion. Therefore, a strap 13 is provided to cinch the upper portion of the boot around the lower leg 12 or ankle, as shown in FIG. 2, in order to produce a liquid-tight compartment inside boot 12. Strap 13 may be fabricated from a Velcro ® material to be readily closed and opened. To assure that this compartment remains liquid-tight the outer surface 27 of boot 10 must be fabricated from a substance which is impervious to the base of the lotions to be used. Suitable materials include a waterproof soft plastic material such as vinyl or fabric treated to be waterproof.

In accordance with the present invention, as shown particularly in FIGS. 3-5, to ensure continuous therapeutic or cosmetic treatment over an extended period a medicament supply network 15 consisting of reservoir 16 and supply fingers 18, 19, 20, 21, 22, 23 and 24 is provided. To emphasize the medicament supply network 15, the outlines of the surface 27 are shown by phantom lines 14. Medicament may be supplied to reservoir 16 as needed through filler tube 17 having a stopper 31. The medicament may be chosen to provide effective treatment for the specific ailment or for the desired cosmetic treatment and may be replenished from time to time. As described subsequently with respect to absorbent lining 28 the medicament should be of appropriate vicosity to flow at the body temperature of the person wearing the boot. The flow is by gravity and capillary action in a downward direction from reservoir 16 into the supply fingers 18, 19, 20, 21, 22, 23 and 24. As the lotion moves through the various fingers a steady supply will be dispensed through the openings 26 into the absorbent lining 28 and thence onto the skin of the foot of the wearer.

As seen in FIGS. 5 and 6 the lotion is supplied adjacent absorbent lining 28 so that the lining is continuously impregnated with the lotion and may transfer it to the skin of the foot of the wearer. Since the lining is absorbent the lotion will move laterally from the openings 26 and maintain substantially all of the absorbent lining in a moist, lotion-impregnated condition. Preferably, the fingers are positioned between impervious outer covering 27 and the absorbent lining 28 so that the foot does not rest against the fingers and experience discomfort and so that the lotion will both pass through the lining and spread laterally to thereby impregnate the entire inner surface of absorbent lining 28 and provide treatment for the entire surface area of the foot. This is shown particularly in FIG. 6 where a portion of the impervious outer covering 27 is broken away at the toe region 9 to disclose absorbent lining 28 and the bottom of finger section 20. The absorbent lining 28 need not have appreciable thickness as it need not store medicament - it only transfers and applies medicament to the foot. Thus, a thin gauze material consisting of fibers 29 is satisfactory. Also satisfactory are a multi-layer mesh structure or very soft absorbent cotton.

The supply fingers 18, 19, 20, 21, 22, 23 and 24 are fabricated from a thin gauge, deformable material that is impervious to and will not degrade in the presence of the lotion and its constituent substances. Apparel grade vinyl is a suitable material. An illustrative finger 30 is shown in partial side view in FIG. 7. The deformable side 25, shown in registration in the cross sectional view in FIG. 8, forms one side of a very low angle elliptically shaped finger. It is not desired to add bulk to the boot so a narrow tube is used and the separation between impervious covering 14 and absorbent lining 28 is not great, as seen in the cross sectional view of FIG. 5 which is in registration with FIG. 4. In one embodiment the holes 26 are located only at the bottom end of the fingers 18, 19, 20, 21, 22, 23 and 24 so as to primarily treat the sole.

In another embodiment, fingers 18, 19, 22 and 23 are omitted and holes 26 are provided only at the bottom of supply fingers 20, 21 and 24 so as to treat primarily the toes or toenails. Or, the entire interior surface area of the boot may be lined with the absorbent lining 28 and the fingers may extend to all regions with the holes 26 supplying medicament to the entire interior surface; the entire foot is thus treated.

In use the boot is worn for extended periods such as during the night or at other leisure periods. It is preferrably worn after the feet have been soaked in warm soapy water and dryed. The lack of bulk allows the boot to be worn under the normal circumstances of life. The reservoir permits the boot to be worn for extended periods without removal for replenishment of the medicament. If replenishment is ever needed or if a new substance were desired then it could be added through the filler tube 17 which is accessible at the opening 11. If desired, the reservoir 16 and the fingers 18, 19, 20, 21, 22, 23 and 24 may be cleaned out by removing the absorbent lining 28 and flowing water or solvent into filler tube 17 and out through holes 26. The absorbent lining 28 may then be replaced or may be replaced whenever desired.

When the boot is used periodically the feet will be soft and free of corns, callouses and other foot conditions that make it uncomfortable to walk or stand. And, the feet have a pleasing appearance when sandals and cut out shoes are worn.

We claim:

1. A boot having a continuous supply of lotion for dermatolgical therapeutic treatment of human foot ailments, comprising:

a boot having an opening shaped to enclose a human foot up to at least about the ankle level, said boot having an integral toe portion and heel portion for accomodating, respectively, the toe and heel of said foot, said boot having an outer covering having an inner and outer surface which is impervious to said lotion;

an absorbent lining of narrow gauge disposed around the inner surface of said outer covering of said boot;

a reservoir having a supply of of lotion affixed to said boot and having an externally accessible opening for receiving said lotion; and a lotion supply network means within said boot between said absorbent lining and said outer covering, said supply network consisting of a plurality of of low angle elliptically shaped hollow supply fingers which extend from said reservoir in fluid communication there of to the extremities of said boot along the inside contours of said outer covering, said supply fingers having openings through which lotion may flow to reach selected areas of said absorbent lining.

2. A boot in accordance with claim 1 wherein said reservoir comprises an annular, liquid tight compartment adjacent said opening of said boot which encircles the ankle of the wearer and is accessible at said opening of said boot.

3. A boot in accordance with claim 2 wherein said reservoir includes a filler tube and stopper which are accessible at the opening of said boot.

4. A boot in accordance with claim 1 wherein said fingers extend to the toe region of said boot.

5. A boot in accordance with claim 1 wherein said fingers extend to the heel region of said boot.

6. A boot in accordance with claim 1 wherein said fingers are positioned between said absorbent lining and said outer covering.

7. A boot in accordance with claim 1 wherein said outer covering is comprised of a vinyl material.

8. A boot in accordance with claim 1 in combination with a supply of lotion within said reservoir, said lotion having a temperature-sensitive viscosity such that it flows out through said openings in said supply fingers at human body temperation.

* * * * *